United States Patent
Takken et al.

(10) Patent No.: US 9,173,782 B2
(45) Date of Patent: Nov. 3, 2015

(54) COORDINATED APERTURED AND EMBOSSED TOPSHEET LAYER MATERIALS, AND ABSORBENT ARTICLES CONTAINING SUCH

(71) Applicant: Kimberly-Clark Worldwide, Inc., Neenah, WI (US)

(72) Inventors: Wendy M. Takken, Alpharetta, GA (US); Hue Scott Snowden, Canton, GA (US); Adrienne R. Loyd, Neenah, WI (US); Heidi B. Hopkins, Neenah, WI (US); Ramona Zenkich, Appleton, WI (US); Katie A. Boland, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 287 days.

(21) Appl. No.: 13/852,450

(22) Filed: Mar. 28, 2013

(65) Prior Publication Data
US 2014/0296815 A1  Oct. 2, 2014

(51) Int. Cl.
*A61F 13/15* (2006.01)
*A61F 13/511* (2006.01)
*A61F 13/512* (2006.01)
(Continued)

(52) U.S. Cl.
CPC ....... *A61F 13/51108* (2013.01); *A61F 13/4756* (2013.01); *A61F 13/5122* (2013.01); *A61F 13/5126* (2013.01); *A61F 13/51104* (2013.01); *A61F 13/51394* (2013.01); *A61F 2013/5127* (2013.01); *Y10T 428/24273* (2015.01)

(58) Field of Classification Search
CPC ............ A61F 13/4704; A61F 13/4756; A61F 13/490001; A61F 13/51104; A61F 13/51108; A61F 13/512; A61F 13/5121; A61F 13/5122; A61F 13/5123; A61F 13/5126; A61F 13/51394; A61F 2013/5127; A61F 2013/51377
USPC .......... 604/382, 383, 385.101; D24/124, 125, D24/126
See application file for complete search history.

(56) References Cited

U.S. PATENT DOCUMENTS

| 3,542,634 A | 11/1970 | Such et al. |
| 3,560,601 A | 2/1971 | Johnson et al. |
| 3,881,490 A | 5/1975 | Whitehead et al. |

(Continued)

FOREIGN PATENT DOCUMENTS

| CN | 3192181 D | 6/2001 |
| CN | 2527254 Y | 12/2002 |

(Continued)

*Primary Examiner* — Lynne Anderson
(74) *Attorney, Agent, or Firm* — Steven D. Flack; Kenya T. Pierre (57) ABSTRACT

A topsheet layer material for use on an absorbent article includes a longitudinal direction, a transverse direction and a depth direction and comprises a planar sheet. The topsheet layer material includes visually and spatially coordinated embossed channels and apertures. The embossed channels are curvilinear indentations configured along either the longitudinal, the transverse direction, or a combination of longitudinal and transverse directions. The apertures are positioned along the topsheet layer material laterally adjacent to the channels such that at least a portion of the apertures have an overall shape configuration that is substantially similar or the same as at least a portion of the shape of the embossed channel. Such coordinated aperture configuration may also be generally concentric with or generally parallel to the embossed channels.

12 Claims, 5 Drawing Sheets

(51) Int. Cl.
*A61F 13/475* (2006.01)
*A61F 13/513* (2006.01)

(56) References Cited

U.S. PATENT DOCUMENTS

| | | | |
|---|---|---|---|
| D240,562 S | 7/1976 | Whitehead et al. | |
| D247,370 S | 2/1978 | Whitehead | |
| 4,079,739 A | 3/1978 | Whitehead | |
| 4,151,240 A | 4/1979 | Lucas et al. | |
| 4,272,473 A | 6/1981 | Riemersma et al. | |
| 4,315,507 A | 2/1982 | Whitehead | |
| 4,342,314 A | 8/1982 | Radel et al. | |
| D276,072 S | 10/1984 | Whitehead | |
| D276,073 S | 10/1984 | Whitehead | |
| 4,591,523 A | 5/1986 | Thompson | |
| 4,609,518 A | 9/1986 | Curro et al. | |
| 4,859,519 A | 8/1989 | Cabe, Jr. et al. | |
| 4,978,486 A | 12/1990 | Ito et al. | |
| 5,370,764 A | 12/1994 | Alikhan | |
| 5,429,630 A | 7/1995 | Beal et al. | |
| D392,736 S | 3/1998 | Erickson | |
| 5,727,458 A | 3/1998 | Schulz | |
| 5,997,986 A | 12/1999 | Turi et al. | |
| D425,985 S | 5/2000 | Mitchler et al. | |
| D426,303 S | 6/2000 | Weyenberg | |
| 6,093,871 A | 7/2000 | Takai et al. | |
| D430,292 S | 8/2000 | Orschel et al. | |
| D430,665 S | 9/2000 | Daniels et al. | |
| D438,958 S | 3/2001 | Velazquez et al. | |
| D439,661 S | 3/2001 | Velazquez et al. | |
| 6,228,462 B1 | 5/2001 | Lee et al. | |
| 6,231,555 B1 | 5/2001 | Lynard et al. | |
| 6,262,331 B1 | 7/2001 | Nakahata et al. | |
| D448,476 S | 9/2001 | Page et al. | |
| 6,319,239 B1 | 11/2001 | Daniels et al. | |
| D478,661 S | 8/2003 | Levy et al. | |
| D482,786 S | 11/2003 | Harriz | |
| D484,973 S | 1/2004 | Costea et al. | |
| 6,911,574 B1 * | 6/2005 | Mizutani | 604/380 |
| 7,056,404 B2 | 6/2006 | McFall et al. | |
| 7,067,711 B2 | 6/2006 | Kuroda et al. | |
| D533,271 S | 12/2006 | Haersjoe | |
| D546,443 S | 7/2007 | Persson | |
| D546,444 S | 7/2007 | Persson | |
| 7,323,072 B2 | 1/2008 | Engelhart et al. | |
| 7,390,553 B2 | 6/2008 | Muth et al. | |
| D581,523 S | 11/2008 | Macaulay et al. | |
| D581,524 S | 11/2008 | Macaulay et al. | |
| D583,466 S | 12/2008 | Dobrin et al. | |
| D583,934 S | 12/2008 | Li et al. | |
| D584,402 S | 1/2009 | Francoeur et al. | |
| D584,403 S | 1/2009 | Francoeur et al. | |
| D594,973 S | 6/2009 | Francoeur | |
| D600,805 S | 9/2009 | Hood et al. | |
| D601,245 S | 9/2009 | Cauwood et al. | |
| 7,628,777 B2 | 12/2009 | Kondo et al. | |
| D607,998 S | 1/2010 | Persson | |
| 7,686,790 B2 | 3/2010 | Rasmussen et al. | |
| D613,856 S | 4/2010 | Mason, Jr. | |
| 8,030,535 B2 * | 10/2011 | Hammons et al. | 604/380 |
| D651,306 S | 12/2011 | Misiti et al. | |
| 8,071,837 B2 | 12/2011 | Saeki et al. | |
| D651,708 S | 1/2012 | Misiti et al. | |
| 8,536,401 B2 * | 9/2013 | Ecker et al. | 604/380 |
| 8,847,002 B2 * | 9/2014 | Goh et al. | 604/378 |
| D715,923 S * | 10/2014 | Cardin et al. | D24/125 |
| 2003/0187418 A1 | 10/2003 | Kudo et al. | |
| 2004/0163783 A1 | 8/2004 | Muller | |
| 2004/0176734 A1 | 9/2004 | Rasmussen et al. | |
| 2005/0124953 A1 | 6/2005 | Woltman et al. | |
| 2006/0087053 A1 | 4/2006 | Odonnell et al. | |
| 2007/0029694 A1 | 2/2007 | Cree et al. | |
| 2007/0087169 A1 | 4/2007 | McFall | |
| 2008/0004581 A1 | 1/2008 | Babusik et al. | |
| 2008/0045915 A1 | 2/2008 | Noda et al. | |
| 2008/0249495 A1 | 10/2008 | Di Virgilio et al. | |
| 2008/0294135 A1 | 11/2008 | Hara et al. | |
| 2009/0026651 A1 | 1/2009 | Lee et al. | |
| 2010/0178456 A1 | 7/2010 | Kuroda et al. | |
| 2010/0230866 A1 | 9/2010 | Gray et al. | |
| 2010/0280471 A1 | 11/2010 | Shah | |
| 2011/0223278 A1 | 9/2011 | Van Valkenburgh et al. | |
| 2011/0319851 A1 | 12/2011 | Kudo et al. | |
| 2012/0088076 A1 * | 4/2012 | Glakpe et al. | 428/195.1 |
| 2012/0265162 A1 | 10/2012 | Kuramochi | |
| 2012/0289917 A1 | 11/2012 | Abuto et al. | |
| 2012/0296304 A1 | 11/2012 | Choo et al. | |
| 2013/0310784 A1 * | 11/2013 | Bryant et al. | 604/385.01 |

FOREIGN PATENT DOCUMENTS

| | | |
|---|---|---|
| CN | 301411655 S | 12/2012 |
| EP | 1 022 007 B1 | 6/2002 |
| EP | 000212212-0001 | 8/2004 |
| EP | 000824313-0001 | 11/2007 |
| EP | 000824313-0005 | 11/2007 |
| EP | 000824313-0007 | 11/2007 |
| EP | 000824313-0011 | 11/2007 |
| EP | 000824313-0012 | 11/2007 |
| EP | 000824313-0014 | 11/2007 |
| EP | 000824313-0018 | 11/2007 |
| ES | 0025203 A | 3/1998 |
| GB | 2089214 A | 6/1982 |
| JP | 2006-181294 A | 7/2006 |
| TW | D125220 S1 | 10/2008 |
| WO | WO 98/51250 A1 | 11/1998 |
| WO | WO 03/103556 A1 | 12/2003 |
| WO | WO 2007/116346 A1 | 10/2007 |
| WO | WO 2011/118473 A1 | 9/2011 |
| WO | WO 2012/044656 A1 | 4/2012 |

* cited by examiner

COORDINATED APERTURED AND EMBOSSED TOPSHEET LAYER MATERIALS, AND ABSORBENT ARTICLES CONTAINING SUCH

FIELD OF THE INVENTION

The present invention relates to topsheet layer materials for absorbent personal care articles. More particularly, it relates to apertured and embossed topsheet layer materials, and the absorbent personal care articles containing such materials.

BACKGROUND

Absorbent personal care articles such as feminine hygiene products, adult incontinence products and baby and child care products often incorporate at least two layers, and more commonly, at least three layers in their structures. For example, sanitary napkins and pads, panty liners, incontinence pads, diapers and bed mats commonly include at least a user-facing topsheet layer (cover layer) for contacting a user's skin, a backsheet layer or baffle, for contacting a user's garments or bedding and for preventing leakage, and an absorbent core layer sandwiched between the topsheet layer and backsheet layer for absorbing and retaining body waste, such as urine, feces and menses. Additional interiorly-situated layers may also be included in the personal care article structure, such as for example, a surge layer, transfer delay layer, or distribution layer positioned between the topsheet layer and absorbent core layer. Alternatively, multiple interiorly-situated layers, such as the aforementioned layers and/or multiple core layers may also be utilized in an article structure.

It is known that such topsheet layer may be of a single layer construction, or of a multiple layer construction (such as a laminate of two or more nonwoven layers) and is commonly embossed either as an individual layer, or in combination with more interiorly-situated article layers. Such embossments (or embossed features) are often employed either to direct or restrict the flow of body exudates along specific paths on the topsheet layer surface, or to affect the flow of such exudate waste into the article core layer(s). An embossing pattern therefore, not only creates in some instances an aesthetically pleasing surface, but the channels may also facilitate intake/movement of menses fluid. Menses will tend to flow along the densified edges of the embossed channels rather than pool on contact points of the topsheet layer. Such embossments are typically formed by compression of the topsheet layer using a pattern/pin and anvil roll set. Heat may also be applied to the pattern roll to fuse the embossed layer materials together. Such embossments are usually in the form of extended channels or discrete points. Examples of such embossments may be found in U.S. Pat. No. 3,542,634 to J. J. Such et al., U.S. Pat. No. 5,370,764 to Alikhan, U.S. Pat. No. 5,727,458 to Schulz, U.S. Pat. No. 6,231,555 to Lynard et al., U.S. Pat. No. 7,067,711 to Kuroda et al., U.S. Pat. No. 7,323,072 to Engelhart et al., and in United States Publications 2003/0187418 to Kudo et al., 2008/0294135 to Hara et al., 2010/0178456 to Kuroda et al., and 2010/0280471 to Shah. It is known that such embossments may slow the flow of waste off of an article's surface along an article's transverse direction/axis by providing enhanced surface area, and a barrier-type structure, as well as specific liquid wicking paths. For example, embossment channels that direct waste to a product's longitudinal ends for absorption into peripheral end regions of a core layer and away from the initial centralized location of article soiling (article central insult region), are often described in the patent literature. Nevertheless, there exists a continued need for a topsheet layer material which allows for targeted waste absorbency/fluid capture and barrier protection. There exists a continued need for a topsheet layer material which assists with the capture of body waste before it flows off of an absorbent article, by providing increased surface area with non-straight embossments. There also exists a need for a topsheet layer material which provides signals to a product user of targeted absorbency/fluid capture features through visually apparent topographical features.

Topsheet layer materials are also often apertured, either via initial layer formation, or through a mechanical, post layer-formation process, so as to create direct channels for body waste to travel from the point of article soiling (insult region) to an interiorly positioned absorbent layer. For example, if such a topsheet layer is a film, such film may be apertured following immediate film extrusion via a vacuum and screen process to create a series of holes or apertures through which waste may eventually flow. Alternatively, film or nonwoven topsheet layers may be apertured or perforated via a mechanical pin, rolling device such as a pin roller set, so as to create relatively larger apertures in a topsheet layer. Examples of these apertures are described for example in U.S. Pat. No. 5,370,764 to Alikhan which is hereby incorporated by reference in its entirety. Even with the wide array of known aperturing methods, there exists a continued need for topsheet layer material aperturing configurations, which may promote targeted/localized and regional absorbency/fluid capture to interiorly situated absorbent layers within personal care articles, and/or which provide a visual signal to a user as to the localized absorbency/fluid capture regions of the article. A further need exists for a liquid-receiving arrangement which provides improved aesthetic appearances to a topsheet layer user-facing surface.

It is known to utilize combination bonding and aperturing patterns with apertures being placed entirely within bonding patterns as for example, those described in U.S. Pat. No. 5,370,764 to Alikhan. It is also known to surround a matrix-style series of apertures with a continuous embossed channel, as can be seen in U.S. Pat. No. 7,067,711 to Kuroda. Finally, it is also known to have curvilinear/wavy embossed features (both in the form of points/dots and channels) on topsheets. See for example, United States publication 2004176734 to Rasmussen et al. and international publication WO 2007/116346 to Di Virgilio et al. However, such embossments do not provide a coordinated visual cue with apertures, to provide a user with multiple visually distinct and targeted/localized, fluid receiving/absorbency features for a topsheet layer. There is therefore a need for aperture and embossment combinations which offer enhanced visual cues of localized absorbency/fluid capture features to a product user. Such features would enhance user confidence in such products.

SUMMARY OF THE INVENTION

A topsheet layer material with coordinated apertures and embossed channel includes a longitudinal direction, a transverse direction and a depth direction. The topsheet layer material includes at least one embossed channel having at least two side edges, and a first series of apertures. The at least one embossed channel has a curvilinear overall shape configuration along either the longitudinal direction, the transverse direction or a combination of longitudinal and transverse directions. The first series of apertures are positioned in an uninterrupted sequence on the topsheet layer material adjacent (such as laterally adjacent) the at least one embossed channel, or a channel portion. The first series of apertures are configured in the same overall shape configuration as at least a portion of the at least one embossed channel overall shape configuration. In an alternative embodiment, such first series of apertures are at least adjacent one side edge of the at least one embossed channel. In an alternative embodiment, a series of visually and spatially coordinated apertures are laterally adjacent at least one side edge of the at least one embossed channel. In one embodiment, such visual coordination shall mean that the aperture overall shape configuration mimics the curvilinear shape of the embossed channel either in its entirety or partially. In one embodiment, such spatial coordination shall mean that the aperture overall shape configuration is immediately adjacent the embossed channel, such as within 2 cm, alternatively, within 1 cm, alternatively less than 5 mm of the embossed channel, such as laterally adjacent.

In one embodiment, the topsheet layer material includes numerous embossed channels, each with coordinated apertures. In one embodiment, the apertures and embossed channel(s) are coordinated visually, that is, they resemble each other in their overall shape configuration, or are the same at least partially, in overall shape configuration and are spatially aligned. In a further alternative embodiment, an embossed channel overall shape configuration may be formed from a single embossed channel, or from proximate separate, embossed channels in a series or sequence, such that they together form an overall shape (as a swirl or circle). In another alternative embodiment, the apertures and embossed channel(s) are coordinated visually and spatially (that is they appear proximate to each other, such as immediately adjacent each other rather than widely separated from one another in different locations on the material). In yet another alternative embodiment, such visually and spatially coordinated apertures and channel are not separated by any other embossed channel. In yet another alternative embodiment of the inventive topsheet layer material, the embossed channel overall shape configuration is selected from a curvilinear shape such as a wave, a swirl, a circle, an oval or other rounded shape. In still a further alternative embodiment, the embossed channel overall shape configuration is a complete shape, such as a circle. Such complete circle may have unconnected ends, such as a series of proximate embossed channels that forms a complete circular shape, or alternatively it may be of a continuous channel configuration. In yet another alternative embodiment, the embossed channel overall shape configuration is an open shape, such as a swirl or partial circle (such as a half circle). In still another alternative embodiment of the invention, the first series of apertures are only visually and spatially coordinated with only a portion of an embossed channel (or partial embossed channel) or vice versa. In still a further alternative embodiment, "substantially" all of an embossed channel curve length is visually and spatially coordinated with a first series of apertures. In one embodiment, the term "substantially" means that at least 51% of the curve length of the embossed channel is adjacent to visually and spatially coordinated apertures and aperture gap spaces (material spaces between the first series of apertures), alternatively, at least 75% of the curve length of the embossed channel is adjacent to visually and spatially coordinated apertures and aperture gap spaces (material spaces between the first series of apertures), in still another alternative embodiment, at least 90% of the curve length of the embossed channel is adjacent to visually and spatially coordinated apertures and aperture gap spaces (material spaces between the first series of apertures).

In still another alternative embodiment of the invention, the topsheet layer material includes a first series of apertures that are at least partially situated (at least an uninterrupted continuous grouping of six apertures) adjacent one side edge of the at least one embossed channel. In another alternative embodiment of the invention, the embossed channel has an end, and the first series of apertures extend around the end of the embossed channel. In still another alternative embodiment of the inventive topsheet layer material, the first series of apertures are present on two side edges (such as two opposed side edges) of an embossed channel.

In yet another embodiment, the topsheet layer material includes an embossed channel having a shape in an open curvilinear configuration and includes at least one side edge. A first series of apertures are situated completely along at least the one side edge of the embossed channel. In still another alternative embodiment, the topsheet layer material includes an embossed channel that has multiple side edges. A series of apertures surround the embossed channel along the multiple side edges, alternatively, completely around the embossed channel side edge or side edges.

In another alternative embodiment of the invention, the topsheet layer material includes an embossed channel having a side edge and the topsheet layer material further includes a first series of apertures that are present in increasing size adjacent the embossed channel side edge. In still another alternative embodiment of the invention, the topsheet layer material includes progressively larger apertures in the first series of apertures, with larger size apertures positioned closest to the embossed channel side edge. In another alternative embodiment of the invention, the first series of apertures extend beyond a side edge of the embossed channel. In still another alternative embodiment, a first series of apertures, desirably of at least six in number, is coordinated with only a portion of an embossed channel side edge. In still another alternative embodiment, the topsheet layer material includes a second set of apertures. In yet another alternative embodiment, the second set of apertures is a matrix of apertures. In still another alternative embodiment, the first series of apertures are each circular in shape. In another alternative embodiment, the topsheet layer material includes embossed channels of different shapes. In still another alternative embodiment, the topsheet layer material includes embossed channels that are concentric to one another. In another alternative embodiment, the topsheet layer material includes embossed channels having different overall shape configurations, each channel having an accompanying coordinated series of apertures. In yet another alternative embodiment, such embossed channel shapes are swirls and circles. In still another alternative embodiment, multiple series of coordinated apertures straddle two side edges (such as two opposed side edges) of a single embossed channel.

In still another alternative embodiment of the invention, the topsheet layer material includes a first series of apertures that are positioned on an embossed channel shape and have a width that extends beyond the width of the embossed channel shape. In still another alternative, the topsheet layer material includes an embossed channel that is coordinated with a first series of apertures substantially along one side edge of the embossed channel. In another alternative embodiment, such embossed channel is completely surrounded by a first series of apertures, at least along one side edge. In still another alternative embodiment of a topsheet layer material of the invention, the embossed channel and coordinated apertures are present in at least one region of the topsheet layer material.

In yet another alternative embodiment, the inventive topsheet layer material is incorporated into a topsheet layer of an absorbent article, such as a sanitary pad, panty liner or incontinence article. In another alternative embodiment, such topsheet layer material is incorporated into only a portion of a multilayered topsheet layer (such as a two layered or dual layered topsheet) of an absorbent article. For example, in one embodiment, the topsheet layer material with coordinated embossed channel and apertures is positioned either along an article longitudinal side edges as side cover layers, or along a central subjacent section of a two-layer topsheet layer, along the article central longitudinal direction.

In still another alternative embodiment of the invention, an absorbent article includes a topsheet layer, a backsheet layer and an absorbent core layer. The topsheet layer and the backsheet layer sandwich the absorbent core layer. The topsheet layer (and absorbent article) includes a longitudinal direction, a transverse direction and a depth direction. The topsheet layer is a planar sheet including embossed channels and a first series of apertures. The embossed channels are of a curvilinear shape configured along either the longitudinal, the transverse direction or a combination of longitudinal and transverse directions of the topsheet layer. The first series of apertures are positioned along the topsheet layer adjacent the embossed channels, such that at least a portion of the apertures have an overall shape configuration that is similar to that of the adjacent channel. Such channels may be swirl, circular, or wavy shape overall shape configurations, for example.

The topsheet layer material of the present invention provides for targeted absorbency/fluid capture regions for directing body exudates into an absorbent article, as well as a visual cue to consumers as to regions of fluid permeability. Objects and advantages of the invention are set forth below in the following description, or may be learned through practice of the invention.

BRIEF DESCRIPTION OF THE DRAWINGS

A full and enabling disclosure of the present invention is set forth more particularly in the remainder of the specification, including reference to the accompanying figures, in which.

DESCRIPTION OF THE INVENTION

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. For the purposes of this application, like features may be represented by like numbers between the figures. While not being expressly illustrated in every view or location, it should be understood that traditional absorbent article construction adhesive is to be used between each of the various article layers, for securement of the layers within the article.

It has been found, that by visually coordinating apertures and embossed channel patterns (embossment features) and spatially aligning such apertures and embossment features within a topsheet layer material (or combination of topsheet layer material and underlying layers) for personal care articles, absorbency of body waste and/or initial capture of fluids (and body exudates) by such articles can be focused in particular localized regions of such articles, as desired. For example, such initial capture of fluids may be visually highlighted to consumers, and accomplished by the creation of drain-like, or sink-like structures formed from the coordinated aperture and embossed channel features. Further, such visually coordinated and desirably spatially aligned aperture and embossed channel patterns provide for increased cues of absorbency/fluid capture pathways to a product user, which could instill higher levels of confidence of proper product placement in a user's undergarment (as such features are readily visible from the topsheet surface), as well as absorbency of the overall product.

Figure 1:
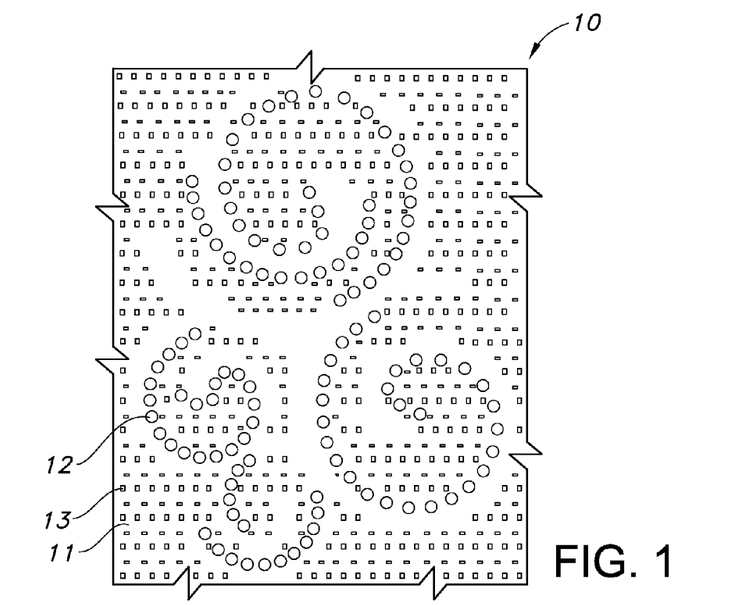
FIG. 1 is a partial top plan view of aperture patterns of a topsheet layer material in accordance with the invention.

In specific reference to FIG. 1, the figure illustrates a partial top plan view of an unembossed topsheet layer material 10 which is manufactured from a planar sheet material 11. Such planar sheet material 11 may be of a single layer material, or alternatively, of multiple layers that have been laminated together to form a unified planar structure. Such topsheet layer material may be formed from numerous materials known in the topsheet layer art, such as for example, one or more fibrous nonwoven sheets, one or more film sheets, such as blown or extruded films, which may themselves be of single or multiple layers, one or more foam sheets, such as reticulated, open cell or closed cell foams, one or more woven sheets, a coated nonwoven sheet, or a combination of any of these aforementioned materials. Such combination may be adhesively, thermally or ultrasonically laminated into a unified planar sheet structure. The topsheet layer material functions to receive and take in fluids, such as urine or menses, and therefore comprises a liquid permeable material as noted. Additionally, topsheet layer materials can further function to help isolate the wearer's skin from fluids held in a subjacent absorbent layer of an absorbent article. It is also well known that one or more chemical treatments can be applied to topsheet layer materials in order to improve movement of the fluid through the topsheet layer and into the article. Suitable topsheet layer materials include, but are not limited to those described in U.S. Pat. No. 4,397,644 to Matthews et al.; U.S. Pat. No. 4,629,643 to Curro et al.; U.S. Pat. No. 5,188,625 Van Iten et al.; U.S. Pat. No. 5,382,400 to Pike et al.; U.S. Pat. No. 5,533,991 to Kirby et al.; U.S. Pat. No. 6,410,823 to Daley et al. and United States Publication 2012/0289917 to Abuto et al., each of which is hereby incorporated by reference thereto in its entirety.

In one desirable embodiment the topsheet layer material may be constructed of any woven or nonwoven material which passes body fluids, yet remains comfortable to the user. Suitable nonwoven materials include, but are not limited to, hydroentangled spunlace materials, bonded carded webs (BCW) made from staple fibers, and spunbond webs. The basis weight of nonwoven webs may generally vary, such as from about 5 grams per square meter ("gsm") to 150 gsm, in some embodiments from about 10 gsm to about 125 gsm, and in some embodiments, from about 25 gsm to about 120 gsm.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, eductive drawing and/or other well-known spunbonding mechanisms. The production of spunbond webs is described and illustrated, for example, in U.S. Pat. No. 4,340,563 to Appel, et al., U.S. Pat. No. 3,692,618 to Dorschner, et al., U.S. Pat. No. 3,802,817 to Matsuki. et al., U.S. Pat. No. 3,338,992 to Kinney, U.S. Pat. No. 3,341,394 to Kinney, U.S. Pat. No. 3,502,763 to Hartman, U.S. Pat. No. 3,502,538 to Levy, U.S. Pat. No. 3,542,615 to Dobo, et al., and U.S. Pat. No. 5,382,400 to Pike, et al., which are each incorporated herein in its entirety by reference thereto for all purposes. Spunbond fibers are generally not tacky when they are deposited onto a collecting surface. Spunbond fibers may sometimes have diameters less than about 40 microns, and often between about 5 to about 20 microns.

Further examples of suitable topsheet materials include rayon, bonded carded webs of polyester, polypropylene, polyethylene, nylon, or other heat-bondable fibers, polyolefins, copolymers of polypropylene and polyethylene, linear low-density polyethylene, and aliphatic esters such as polylactic acid. Other suitable topsheet layer materials include through-air bonded carded webs (TABCW) made from staple length fibers such as a 25 gram per square meter (gsm) web made with 1.5 denier (d), polyethylene sheath, polypropylene core bicomponent, 35-40 millimeter (mm) staple length fibers available from FiberVisions Corporation with offices in Duluth, Ga., USA which are available under the trade designation ESC215.

Figure 3:
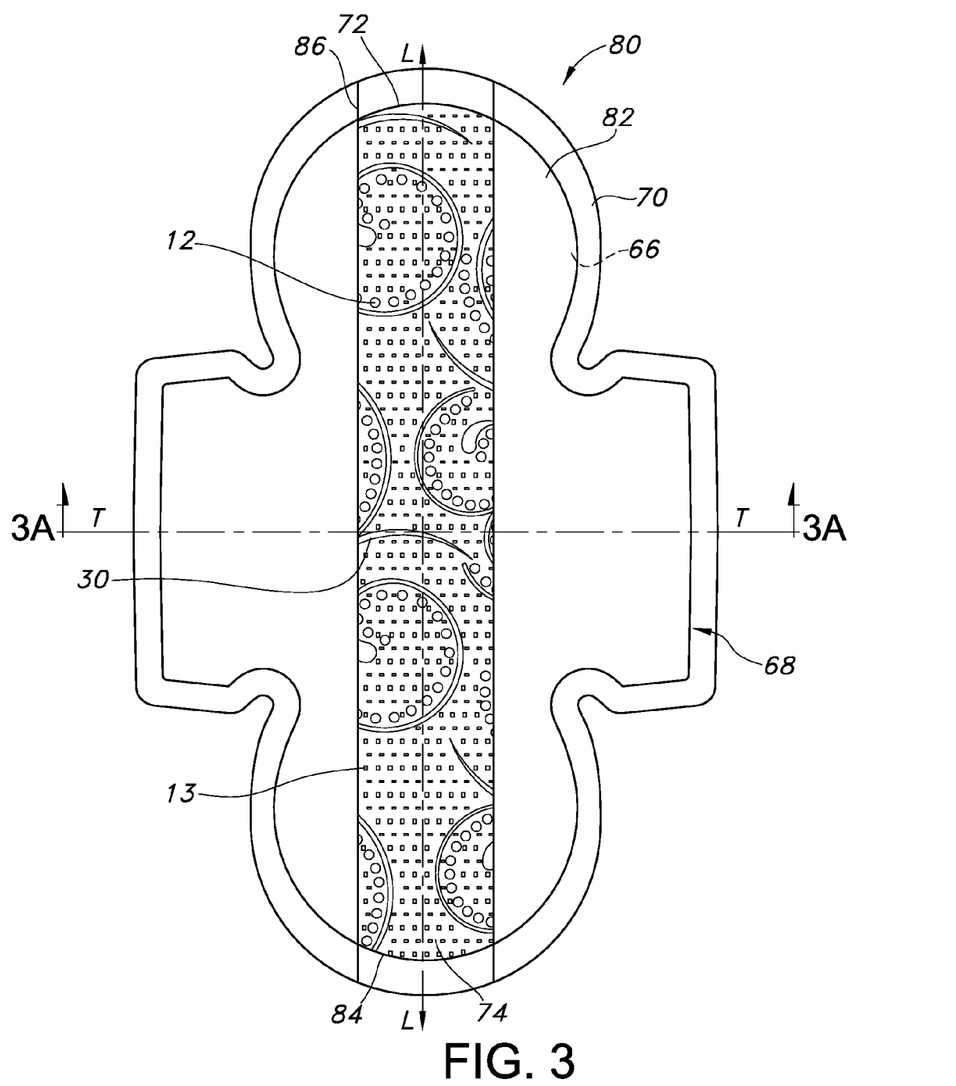
FIG. 3 is a top plan view of still another alternative embodiment of a feminine sanitary pad employing a coordinated aperture and embossed channel pattern of a topsheet layer material in accordance with the invention.

The topsheet layer material may also be made from two or more different nonwoven or film materials, with the different materials placed in separate locations laterally across the topsheet layer. For example, the topsheet layer may be a two layer (in two depth direction planes) or multi-component material with a central section (as illustrated in FIGS. 3-4A) positioned along and straddling the longitudinal center direction of the product, with lateral side-cover sections flanking and joined to each side (or side edge) of the central section. The central section may be made for example, from the aforementioned TABCW materials or it may be made from a perforated film. The lateral side sections may be made from a different fibrous nonwoven material which is joined to the central longitudinally directed section. Such a two layer (also known as dual cover) configuration is described for example, in U.S. Pat. No. 5,961,505 to Coe, U.S. Pat. No. 5,415,640 to Kirby and U.S. Pat. No. 6,117,523 to Sugahara, each of which is hereby incorporated by reference in its entirety. Such a two layer topsheet material (or bicomponent topsheet) can offer the feeling of dryness in the center longitudinally direction section, and a soft feeling along the side longitudinally directed sections. It is also contemplated that such two layer topsheet materials may additionally include elastic components along their side edges to lift up portions of the side materials during use, thereby forming physical barriers or cupping features on the product so as to fit more closely to the body of a user.

Such topsheet layer material includes a pattern of, or first series of apertures 12 which are desirably placed in an overall shape configuration that is curvilinear. For the purposes of this application, the term "apertures" shall not refer to the random interstitial/interfibrous gaps/spaces normally formed between fibers or filaments of a nonwoven or woven planar sheet during initial sheet deposit on a forming wire, or from weaving. As illustrated in the figure, the first series of apertures are shown in overall shape configurations that resemble swirls or partial swirls. The term "overall shape configuration" shall mean the shape formed by an uninterrupted series/sequence of apertures, or multiple relatively-short embossment channels) which sequence (in the case of apertures or short channels) forms a relatively larger coherent shape, when compared to the individual apertures or channels themselves. The series/sequence of apertures or short embossment channels are desirably visually recognizable as part of a coherent larger shape, when viewed from a distance of at least one foot, more desirably, when viewed from a distance of at least two feet, still even more desirably, when viewed from a distance of at least three feet. The individual apertures themselves, of an overall shape configuration of apertures, may be of any individual shape, or of different shapes, although in FIG. 1 they are illustrated as all circular in shape. Such individual apertures may be for example, all of oval, circular, triangular, hexagonal, polygonal, rectangular, square or other geometric shapes or of a combination of such. Such aperture opening shapes or short embossment channel shapes, may be uniform or nonuniform in a series, and may be equally spaced apart from each other, or nonuniformly spaced apart from one another. For example, as can be seen in the overall swirl shape configuration series of apertures in the upper portion of FIG. 1, the material spaces or gaps between adjacent circular apertures vary along the overall swirl shape configuration. It is desirable for such individual adjacent apertures to be in one embodiment, uniformly spaced apart from one another and of one geometric shape type. In a second embodiment, it is desirable for such individual adjacent apertures to be spaced less than 1 centimeter (cm) apart. In a further embodiment, such adjacent individual apertures should be spaced less than 5 millimeters (mm) apart. In a further alternative embodiment, such adjacent aperture geometric shape types may be the same in an overall shape configuration, but of different sizes, such as progressively larger or smaller, adjacent a side edge of an embossed channel. Further, such apertures may be present in a shape configuration that is a generally "complete" overall shape configuration, such as arranged in a complete circular shape, or alternatively, in an "open" overall shape configuration, such as a partial circle with irregularly, large-spaced material gaps between apertures, or the swirl shapes as illustrated. Similarly, an embossed channel overall shape configuration may be formed from one extended embossed channel or from proximate but separated, embossed channels in a series or sequence, such that they together form an overall shape configuration (as the swirl seen in the left swirl feature of FIG. 1A). As shown in FIG. 1, such topsheet layer material may also optionally include at least one additional set of apertures 13, for example, placed along a matrix within the material to provide for additional permeability of the topsheet layer material. As shown, such additional set of apertures may include one or more shapes, and may be in a regular, repeating pattern, or in a non-regular, pattern. If present in a topsheet layer material, such matrix (or set of non visually coordinated apertures), should be visually distinguishable from the first series of apertures that are in a curvilinear overall shape configuration. For example, such first series of apertures are distinguished from the matrix of apertures in FIG. 1, by aperture shape, size, and/or spatial configuration.

Each of the apertures contained in the topsheet layer material may be formed from the same or different aperture-forming processes, such as through the previously noted mechanical puncturing techniques (pin and anvil roll aperturing) or through other non-random hole-forming processes, such as for example, through needling, waterjet perforation, vacuum aperturing, or other known targeted melt-forming techniques. As noted, the apertures may vary in shape, size, depth and overall distribution/placement on the topsheet layer material. For example, some regions of the topsheet layer material may include the first series of apertures and coordinated embossed channels, while others will not. Such first series of apertures in a curvilinear overall shape configuration may be placed only along the central longitudinal direction of the topsheet layer material. Individual aperture diameters may in one embodiment range from about 0.1 mm to about 5 mm, from about 0.4 mm to about 1.5 mm or from about 0.5 to about 1.0 mm. In a desirable embodiment, the individual apertures and first series of apertures are both easily visible to a user (such as for example, from a viewing distance of 1 foot). The aperture density if a matrix-type aperture pattern if present, may in one embodiment range from about $7.8 \times 10^3$ holes/m$^2$ to about $1.9 \times 10^6$ holes/m$^2$, from about $4.7 \times 10^4$ holes/m$^2$ to about $9.3 \times 10^5$ holes/m$^2$ or from about $1.6 \times 10^5$ holes/m$^2$ to about $3.1 \times 10^5$ holes/m$^2$. The apertures may extend through the topsheet layer material only, or through the topsheet layer material and more interiorly-situated absorbent article layers as well.

Figures 1A, 1D:
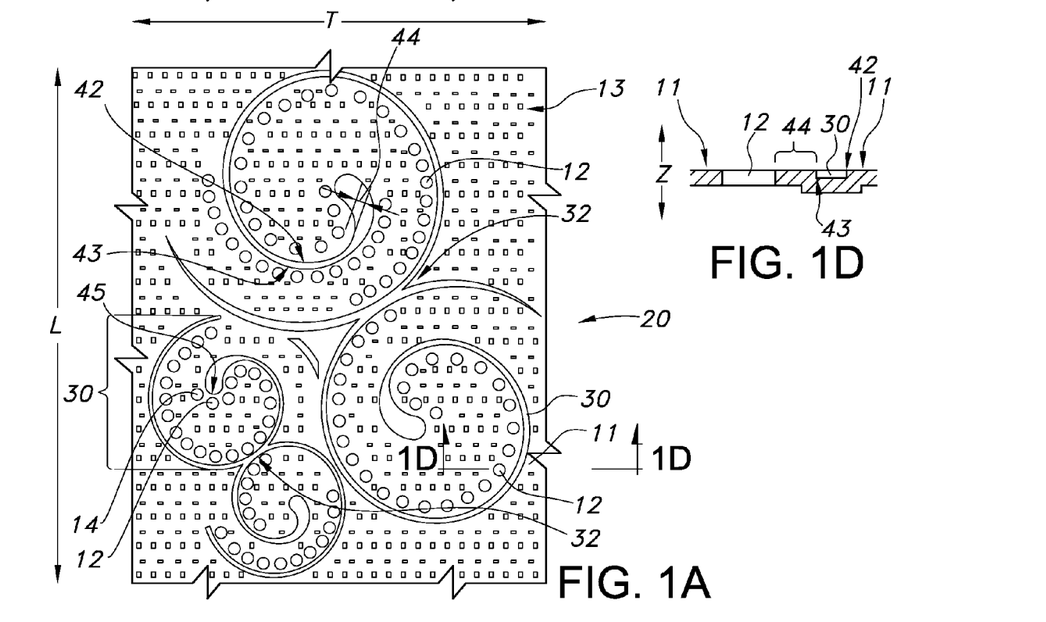
FIG. 1A is a partial top plan view of coordinated apertures (such as those from FIG. 1) and embossed channel patterns (embossment features) of a topsheet layer material in accordance with the invention.
FIG. 1D is a partial cross-sectional view along line 1D-1D of the topsheet layer material of FIG. 1A, illustrating a coordinated aperture and embossed channel pattern in the Z (depth) direction.

As can be seen in FIG. 1, swirl-shaped void spaces (areas having no apertures) within the planar sheet of the topsheet layer material 10 lie immediately, laterally-adjacent to the first series of apertures 12, to allow for the placement of visually coordinated embossment features (embossment channels) in the inventive material, that are desirably spatially aligned with the first series of apertures. Such visually coordinated embossment features are desirably placed at least laterally adjacent to the first series of apertures, such as along the transverse direction (as seen in FIG. 1A). In one embodiment, such first series of apertures are positioned partially adjacent to the embossment channels, such that there is only partial lateral overlap of the apertures in the series along side the accompanying, visually coordinated embossment channel.

As can be seen in the partial top plan view of FIG. 1A, a topsheet layer material of the present invention 20 (the sheet materials described with respect to FIG. 1) includes a longitudinal direction "L", a transverse direction "T" and a depth direction "Z" (as seen in FIG. 1D) in the planar sheet material 11. The visually and spatially coordinated embossed channel pattern and apertures may extend primarily in the longitudinal direction, primarily in the transverse direction or in a combination of both directions. The topsheet layer material of the present invention 20 includes a first set or series of apertures 12, previously exemplified in FIG. 1, and also includes a coordinated embossed channel feature or embossed pattern 30 laterally adjacent to, and of a similar or the same, overall shape configuration to the overall shape configuration of the first series of apertures 12 or alternatively, a portion of the first series of apertures (at least six apertures). Alternatively, a first series of apertures 12 (at least six apertures) may have a similar or the same, overall shape configuration as a coordinated embossed channel, or a portion of the embossed channel. Hence the coordination of apertures to embossment channel features or pattern refers to desirably both visual and spatial coordination. Desirably such embossment feature(s) 30 is in the form of one or more curvilinear embossment channel shapes, such curvilinear shapes being complete or open shapes, shapes such as swirls, waves, ovals, circular or other rounded configurations. Such embossed channels are desirably situated immediately, and laterally adjacent to a first series of apertures 12 such that they are only slightly lateral to the apertures. The first series of apertures are desirably, in one embodiment, entirely outside of the coordinated embossed channels. In this fashion, two separate fluid capture/control features are positioned across a relatively large surface area of the material. The embossment channels are desirably aligned with the apertures. For example, it is in one embodiment desirable for the closest edge-to-edge distance 44 between the embossed channel (or pattern) 30 and the first series of apertures 12 to be less than about 2 cm. That is, the distance 44 between each aperture side edge in the first series of apertures, and the closest point on the coordinated embossed channel side edge, to be less than about 2 cm. In a second embodiment, it is desirable for the distance (separation distance) to be less than about 1 cm. In still a further embodiment, it is desirable for the separation distance to be less than about 5 mm. In still a further embodiment, it is desirable for the separation distance to be between about 1 and 5 mm. In yet another alternative embodiment, such distance should be less than about 2 mm. In still another embodiment, such first series of apertures is situated on the embossed channels, such that at least each aperture in the first series 12, has an edge that extends away from the channel side edge (outside of the embossed channel) by a distance of less than about 5 mm. Essentially in such an embodiment, as is illustrated in FIG. 1C to be described, the diameter or widths of each aperture is larger than the width of the coordinated embossed channel.

By having the two absorbency/liquid capture features present in such close proximity, it is theorized that such features (depending on aperture and embossment size, placement, shape and depth) can provide visually recognizable and targeted absorbency/fluid capture regions in a topsheet layer material. It is desirable in one embodiment, for each of the embossment features (such as each swirl or curvilinear shape) to include its own visually and spatially coordinated series of apertures, and in some instances as illustrated, multiple sets of visually and spatially coordinated apertures (uppermost swirl feature in FIG. 1A). In still a further embodiment, all apertures within the topsheet layer material are visually and spatially coordinated with an adjacent embossment feature. It is desirable in one embodiment for such spatially coordinated series of apertures to be located laterally proximate to the embossed channel, desirably immediately, laterally adjacent the embossed channel (without any other aperture feature between them), as opposed to widely separated from the embossed channel. Widely separated being in one embodiment, greater than a 3 cm separation distance between each of the apertures in sequence (series), to the closest point on the embossed channel. Desirably, in an alternative embodiment, such coordinated first series of apertures and embossed channel, do not have an aperture, or a second, non-similar (visually), embossed channel or other embossed feature between them.

Desirably, such first series of apertures is a continuous, uninterrupted series or sequence of apertures laterally adjacent at least one side edge of an embossed channel. Desirably in one embodiment, such first series or apertures are uniformly spaced from the embossed channel feature along one side edge of the channel. As an example, as can be seen in FIG. 1A, the uppermost illustrated swirl embossment channel 30, includes a first outwardly facing side edge 42 and a second outwardly facing side edge 43. As can be seen in the noted swirl-shaped channel, a continuous, uninterrupted series or sequence of apertures are present laterally from, and along each of the two opposed side edges. For the purposes of this application, the term "uninterrupted" shall mean a series or sequence of apertures positioned along a curvilinear path, laterally adjacent a side edge of the coordinated curvilinear embossment feature (such as an adjacent series of embossed discrete dots, short channels, or an embossed continuous channel), and without the series/sequence of apertures being separated into two or more isolated series of apertures along the side edge of the coordinated embossment feature, by either a portion of the coordinated embossed channel (or feature) that loops between them, or by any other noncoordinated embossment feature. Such uninterrupted series are illustrated by the visually and spatially coordinated swirl channel embossing and aperture features shown in each of the swirl features of FIG. 1A, and with the largest uninterrupted aperture series, on the top coordinated swirl feature illustrated in FIG. 1A. Multiple uninterrupted series of apertures may be coordinated with one embossed feature or channel. For example, one embossed channel may be visually and spatially coordinated with a first series of apertures and a second series of apertures, as seen in FIG. 1A uppermost and lowermost swirl features. For the purposes of this application, an embossed channel is an embossment feature in which the length of the embossment feature exceeds its width, desirably by at least two times. In one embodiment, embossment/embossed features are desirably channels.

Figure 1B:
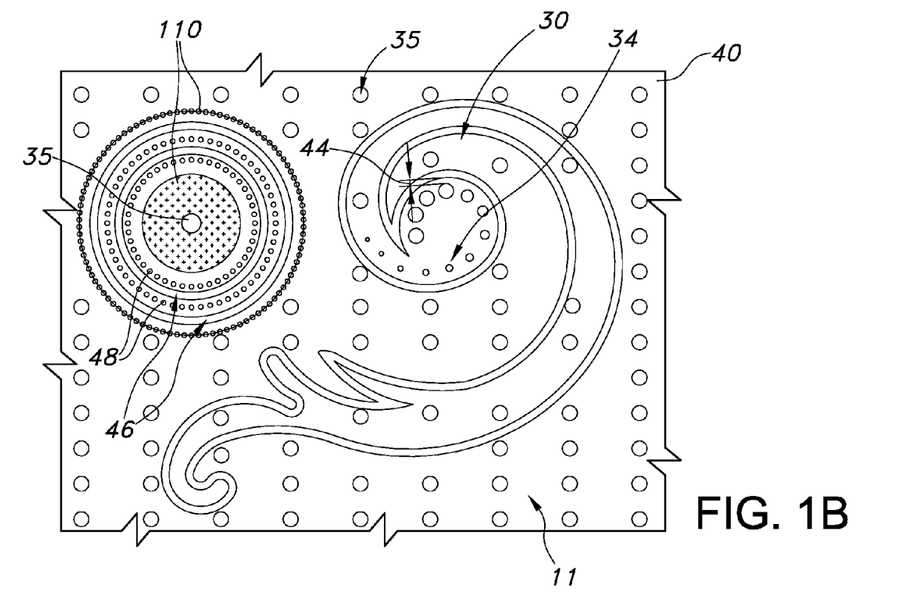
FIG. 1B is a partial top plan view of an alternative embodiment of coordinated aperture and embossed channel patterns of a topsheet layer material.
Figure 1C:
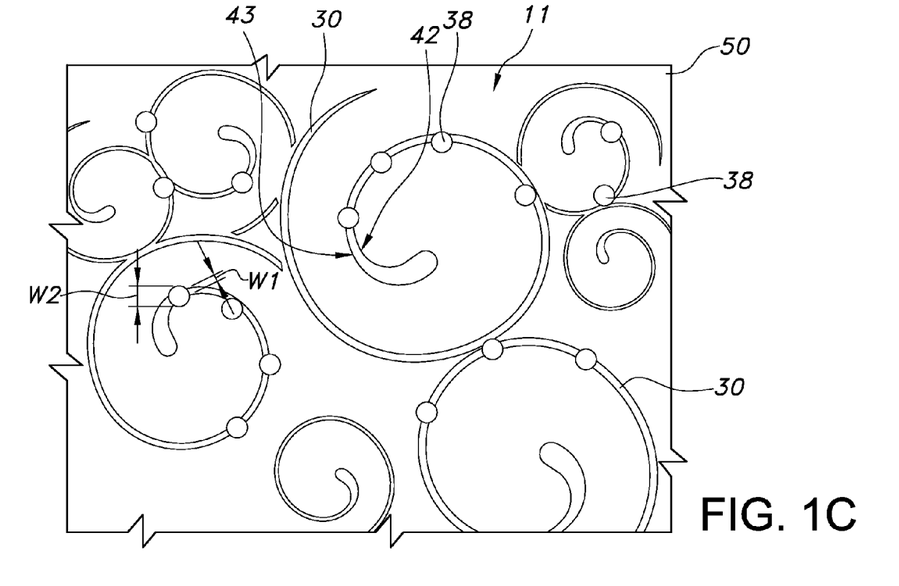
FIG. 1C is a partial top plan view of still another alternative embodiment of coordinated aperture and channel embossed patterns of a topsheet layer material.

Still in a further alternative embodiment, such first series of coordinated apertures may partially overlap with the embossed channel itself, but have a width dimension that extends beyond the width dimension of the embossed channel feature, such as that series of coordinated apertures 38 shown in FIG. 1C. The embossed channel 30 and series of apertures 38, are desirably coordinated even in the overlapping configuration of FIG. 1C, such that that they each are present in the material in an overall visually similar or identical shape configuration, and in the case of FIG. 1C, an overlapping swirl configuration. The overall shape configuration of the aperture series mimics the shape of the accompanying embossed channel. The first series of apertures 38 in FIG. 1C are partially, laterally adjacent to the embossed channel. In FIG. 1A, the first series of apertures 12 are entirely, laterally adjacent to the embossed channels.

In one embodiment of the invention, the first series of apertures are only visually and spatially coordinated with only a portion of an embossed channel or vice versa, such as having six or more apertures of a first series visually and spatially coordinated with a portion of an embossed channel. In still a further alternative embodiment, "substantially" all of an embossed channel curve length is visually and spatially coordinated with a first series of apertures. In one embodiment, the term "substantially" means that at least 51% of the curve length of the embossed channel is laterally adjacent to visually and spatially coordinated apertures and aperture gap spaces (topsheet layer material spaces between adjacent first series of apertures), alternatively, at least 75% of the curve length of the embossed channel is adjacent to visually and spatially coordinated apertures and aperture gap spaces (topsheet layer material spaces between adjacent first series of apertures), in still another alternative embodiment, at least 90% of the curve length of the embossed channel is adjacent to visually and spatially coordinated apertures and aperture gap spaces (topsheet layer material spaces between adjacent first series of apertures).

Generally, in a desirable embodiment, the first series of apertures 12 may partially surround the embossed channel or feature 30, or alternatively, may straddle one, or both outwardly directed side edges of the embossed channel pattern as illustrated in FIG. 1A (uppermost illustrated swirl feature). It is also contemplated that certain apertures 14 in the first series of apertures 12 may partially surround a relative end 45 of the embossed channel feature 30, such that they extend from one side to the other of the embossed channel feature 30, if the embossment feature is an open ended feature such as a swirl. While it is not shown in FIG. 1A, it is also contemplated for a first series of apertures to completely surround a coordinated embossment feature, such as an embossed channel. Such is shown at 46, 48 in FIG. 1B which illustrates a complete circle of apertures around a complete embossed circular channel. It is contemplated in one embodiment of the inventive material of the invention, for one or more embossment channel features to intersect such that two or more curvilinear shapes 30 intersect 32 at a particular region or regions on the embossment pattern. In still a further alternative embodiment, separate groupings of apertures may be present in a first series such that separate uninterrupted groupings of apertures appear along the same side edge of an embossment channel feature, or portions of an embossment channel feature. Such is illustrated for example, in the bottom illustrated swirl of FIG. 1A, in which one uninterrupted grouping of apertures is present towards the swirl middle location, while another is positioned at the swirl opening location. For the purpose of this application, each grouping of apertures in a series desirably includes at least three or more individual apertures. In a further alternative embodiment, each grouping of apertures in a coordinated series desirably numbers six or more. In still a further alternative embodiment, each grouping of apertures in a coordinated series desirably numbers 10 or more. It should be generally recognized that the larger the number of coordinated apertures in a grouping, the more similar the overall shape configuration of the first series of apertures is to the accompanying/coordinated embossment feature (or channel), and the more visually apparent the targeted absorbency/fluid capture region is to a potential consumer. While the topsheet layer material shown in FIG. 1A includes a second set of apertures in a regularly spaced matrix of differently sized rectangles 13, such second set is not necessary for the practice of a topsheet layer material 20 of the invention.

As can be seen from FIG. 1A, it is desirable for the aperture overall shape configuration of the first series of apertures to closely conform with the embossment feature shape. In one desirable embodiment, such aperture overall shape configuration is approximately concentric with the embossment channel shape, or parallel with the embossment channel shape. In an alternative embodiment, a first series of coordinated apertures may be positioned adjacent a second series of coordinated apertures without being separated by an embossment feature, as seen with the relatively large circular apertures towards the middle of the upper swirl feature illustrated in FIG. 1A. In still another alternative embodiment, a first series of coordinated apertures may be positioned entirely adjacent a single side edge of an embossment channel feature, as seen in the swirl positioned on the right side of FIG. 1A. In still a further alternative embodiment, a first and second series of coordinated apertures may be positioned on opposing side edges of two intersecting embossment features, as seen along the intersecting swirl features on the lower left portion of FIG. 1A. While it is desirable to coordinate a lengthy, continuous uninterrupted series of apertures with an embossed channel feature, in which the continuous uninterrupted series of apertures is positioned along the same side edge of the embossed channel feature, it is contemplated in an alternative embodiment, to position shorter, uninterrupted series of apertures along one side of a coordinated embossed channel feature with a space separating the shorter uninterrupted series ((and in which no other stray, similarly sized aperture, or embossed feature (loop or noncoordinated)) is present. It is desirable in one embodiment for at least two uninterrupted series of coordinated aperture groupings of at least six apertures, to be positioned along the same side of a curvilinear embossed channel feature. Such is illustrated in the lowermost coordinated aperture and embossed swirl feature of FIG. 1A (in which a gap exists between each grouping of similarly sized coordinated apertures that are located on the same side of the embossed channel feature). As can be seen in the upper swirl feature of FIG. 1A, in an alternative embodiment, a coordinated series of apertures adjacent one of the channel side edges 43, is coordinated with only a portion of the embossed channel shape (curve length), rather than all, or substantially all of the channel shape (curve length).

A partial top plan view of an alternative embodiment of the inventive topsheet layer material is illustrated in FIG. 1B. Such alternative topsheet layer material 40 includes multiple different embossment features 30, 46 such as a swirl-shaped embossment channel 30 as part of an overall paisley-like channel embossment feature, and complete, circular embossment channel features 46. Although, two such concentric circular embossment channel features are illustrated in FIG. 1B, more concentric embossment channel features are within the scope of the contemplated inventive material. The topsheet layer material 40 of FIG. 1B also includes a first series of coordinated apertures 34 having progressively smaller aperture sizes from the center of the swirl channel embossment feature to the outer portions of the swirl. Such size progression provides additional visual cues to a consumer of the absorbent/fluid capture features of the topsheet layer material. As exemplified by this first series of apertures, such apertures are coordinated with the overall curvilinear/swirl embossment shape 30, but may also include apertures of differing sizes and of different separation distances between apertures, and from the embossment channel feature itself. While including progressively smaller sizes, such first series of coordinated apertures are still clearly visually and spatially coordinated with the laterally adjacent embossment channel feature shape 30, as opposed to being merely surrounded by the confines of a closed embossment channel shape. Such coordination is in part occurring as a result of the close proximity of the apertures to the embossment channel shape, and the mimicking of overall shape configuration. As noted, a second embossment channel pattern in the form of two concentric circles 46 is also shown in FIG. 1B. A second and third series of coordinated apertures, in the form of overall complete and concentric circular configuration shapes (of individual circular apertures) is shown 48 completely surrounding the smaller of the inner concentric circular embossment channel. In order to provide additional visual emphasis (visual cue) to the coordinated embossment channel and aperture features, printing features are also included in the illustrated embodiment 110 of FIG. 1B. Such printing features may be placed on either side of the topsheet layer material to enhance the visual cue of a targeted absorbency region, using known printing techniques, such as for example, ink jet, gravure, and flexographic printing methods. Further, a third set of apertures in the form of a matrix of circles 35 is also present in the topsheet layer material 40 so as to provide additional openings for either liquid or vapor permeability. Multiple sets of apertures are desirable for traditionally liquid impermeable sheet materials, such as polymeric film sheets, or certain smaller fiber diameter, hydrophobic nonwoven sheet materials, such as those containing meltblown fibers.

As noted, a further embodiment of the inventive topsheet layer material 50 is illustrated in the partial top plan view of FIG. 1C. As can be seen in the Figure, the topsheet layer material includes swirl-like embossment features 30 in the planar sheet material 11, having a width W1. A first series of relatively larger circular apertures 38 are coordinated with the embossment features, 30 in a swirl like pattern, but instead of the first series of larger circular apertures 38 being completely offset from and entirely adjacent to the embossment features 30, they are positioned over the embossment features such that a portion of their width dimension W2 extends laterally beyond the width dimension W1 of the embossment features 30. In this embodiment, a dimension of the apertures W2 is larger than that of the embossment feature W1. Essentially, the diameter of the aperture holes is larger than the width of the embossed channels, such that they are partially, laterally adjacent to the embossed channels. As with the previous embodiments, the overall shape configuration of the apertures is coordinated with the embossed channel shapes to both focus permeability/absorbency features in particular areas along the topsheet layer material surface, and also to provide visual emphasis of these areas (in the form of visual cues) to consumers. In this embodiment, only a portion of the apertures extend outside the area of embossment features whereas in prior illustrated embodiments, the entirety of the coordinated apertures are positioned outside of the area of coordinated embossment features. Also of note, in the embodiment illustrated in FIG. 1C (as also in FIG. 2), no additional aperture set is shown, other than the coordinated apertures, although one can be included if desired. For the purposes of the inventive topsheet layer material, in which the planar sheet is a film or film laminate, it is desirable to include at least a first and second series of apertures, at least one of which is a coordinated series of apertures (as shown in FIG. 1A). In such an instance, given the relatively low liquid permeability of most polymeric films, having multiple series of apertures at least one of which would be coordinated with an embossment feature, would enhance the overall liquid permeability of the film. However, if such inventive topsheet layer material is formed from a nonwoven or woven material, the necessity of including numerous distinct series/sets of apertures (some of which are not coordinated with embossment features) is reduced, given the normal interstitial spaces between fibers of a nonwoven or woven material, which often results in higher levels of permeability than polymeric films.

In an enlarged, partial cross-sectional view of the topsheet layer material of FIG. 1A, as seen in FIG. 1D taken along line 1D-1D, the planar topsheet material 11 includes distinct apertures 12 positioned immediately, laterally adjacent to embossment features 30 (channels), which are compressed areas of the planar sheet material 11. The illustrated aperture and embossment features of FIG. 1D are immediately adjacent as no other aperture or embossment features separates them. The visually and spatially coordinated aperture and embossed features of the inventive topsheet layer material may be placed on the topsheet layer material either in separate, individual process steps, such as for example, via a separate embossment roll set and mechanical, pin aperturing roll set, or as part of a single process in which a roller set imparts both apertures and embossment features in the same material as it passes through such roll set. As noted with respect to apertures, the embossment feature may be placed in the topsheet layer material itself, or alternatively in both the topsheet layer material and at least one underlying layer (not shown) positioned between the topsheet layer and the backsheet layer.

Absorbent personal care articles in the form of feminine sanitary pads which include the inventive topsheet layer material, are illustrated in FIGS. 2 through 4A in a flat and unfolded state. Except as otherwise noted, discussion of dimensions of the article and/or the positions of individual components thereof are in reference to the article being in a flat and unfolded state. While feminine hygiene articles (sanitary pads) are illustrated, it should be understood that many types of absorbent articles, such as diapers, training pants, incontinence articles such as briefs and pads, bed mats and bandages, can utilize the topsheet layer material of the invention. Such topsheet layer material is particularly useful in an absorbent article having at least a topsheet layer, a backsheet layer, and an absorbent core layer sandwiched between the topsheet layer and backsheet layer. As used herein, the terms "comprising" or "including" are inclusive or open-ended and do not exclude additional unrecited elements, compositional components, or method steps. Accordingly, the terms "comprising" or "including" encompass the more restrictive terms "consisting essentially of" and "consisting of."

Figure 2:
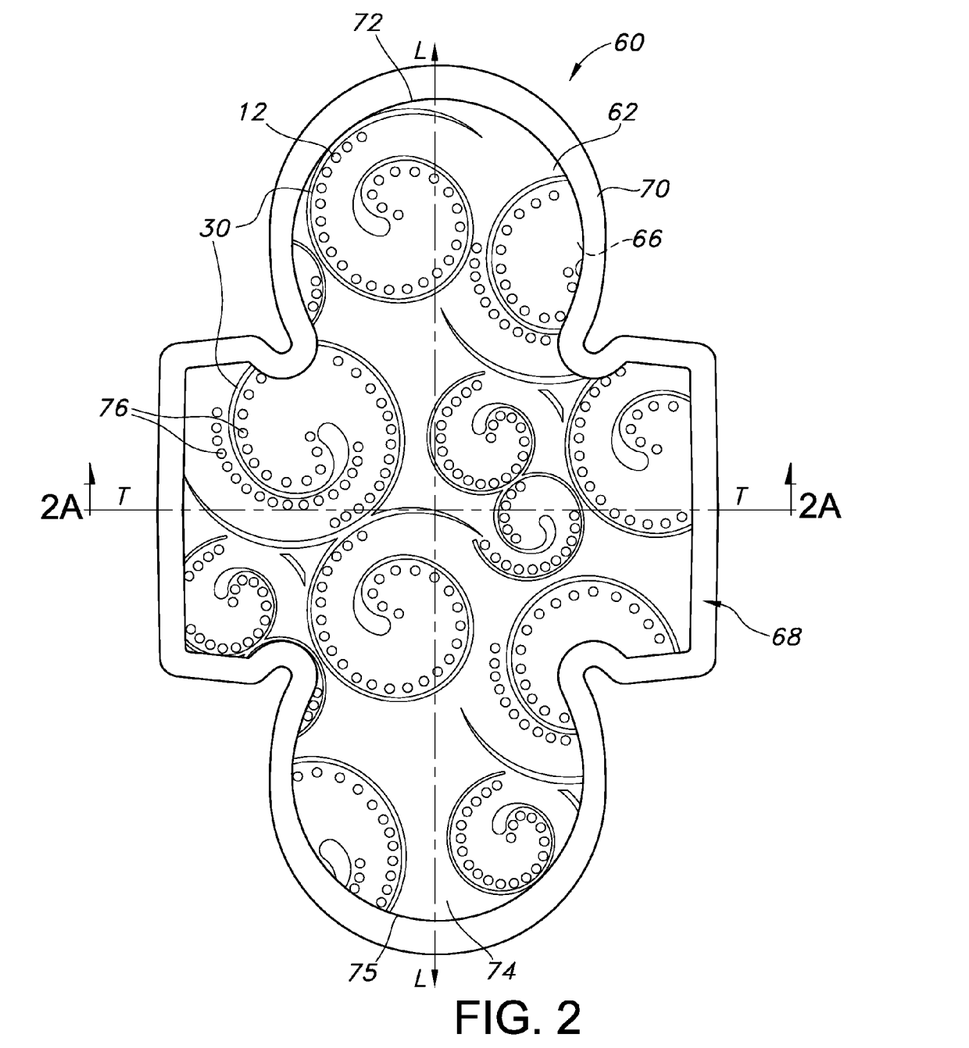
FIG. 2 is a top plan view of an absorbent article in the form of a feminine sanitary pad in accordance with the invention, including a topsheet layer material having coordinated apertures and embossed channel patterns.
Figure 2A:
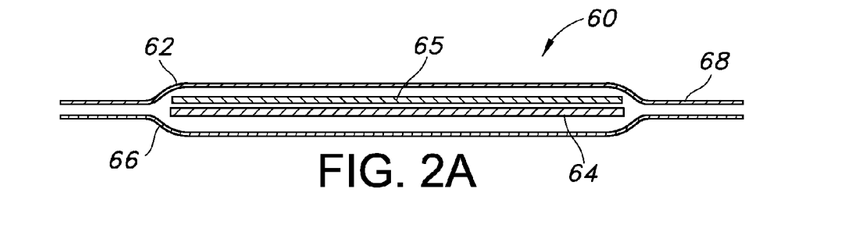
FIG. 2A is a stylistic cross-sectional view of the feminine sanitary pad of FIG. 2 taken along line 2A-2A of FIG. 2.

In reference to FIGS. 2 and 2A, a top plan and stylistic cross-sectional view respectively, are shown of an absorbent article in the form of a feminine sanitary pad 60. The feminine sanitary pad includes a longitudinal direction L and a transverse direction T. Such pad includes longitudinally directed side edges comprising two outwardly extending wings or flaps 68 originating from the main body of the pad, which wings are to be used to wrap the pad around a user's undergarments for securement of the pad to such undergarments. A first longitudinal end 72 and a second longitudinal end 75 are included in the pad. A central longitudinal region 74 on the topsheet layer is situated along the longitudinal direction of the pad. The pad is illustrated including a topsheet layer material of the invention. With respect to the general function and structure of the feminine sanitary pad 60, the user-facing topsheet layer 62 is shown with a visually and spatially coordinated aperture and embossed channel pattern in the form of curvilinear, open swirls. As previously described, the topsheet layer material includes embossment features 30 that are coordinated with a first series of apertures 12. Some of the apertures are illustrated as appearing on only one side edge of an embossment feature, while other embossment features have series of coordinated apertures on both opposed side edges 76. Such liquid permeable, user-facing topsheet layer material is bonded at least at its periphery, to the garment-facing, backsheet layer or outer cover layer 66, at a peripheral seal region 70. Such peripheral seal region may be formed by any known bonding technique, such as for example ultrasonic, adhesive or thermal bonding methods. Such bonding region typically compresses and seals the topsheet layer to the backsheet layer. The outwardly facing surface of the topsheet layer 62 will eventually come in contact with the body of a user, while the outwardly facing surface of the backsheet layer 66 will eventually come in contact with garments or bedding of a user.

The backsheet layer 66 or outercover, functions to isolate absorbed fluids from the wearer's garments or bedding, and therefore desirably comprises a liquid-impervious material. In one aspect, the backsheet layer 66 may optionally comprise a material that prevents the passage of liquids but allows air and water-vapor to pass there-through. The backsheet layer can comprise a single layer or multiple layers, and these one or more layers can themselves comprise similar or different materials. Suitable backsheet layer materials include, but are not limited to, polyolefin films, nonwovens and nonwoven laminates, and film/nonwoven laminates. The particular structure and composition of the backsheet layer 66 may be selected from various known films and/or fabrics with the particular material being selected as appropriate to provide the desired level of liquid barrier, strength, abrasion resistance, tactile properties, aesthetics and so forth. Suitable backsheet layer materials include, but are not limited to, those described in U.S. Pat. No. 4,578,069 to Whitehead et al.; U.S. Pat. No. 4,376,799 to Tusim et al.; U.S. Pat. No. 5,695,849 to Shawver et al; U.S. Pat. No. 6,075,179 et al. to McCormack et al. and U.S. Pat. No. 6,376,095 to Cheung et al., each of which are hereby incorporated by reference thereto in its entirety. While not shown in the figures, it is known in the art that such pad may also include patches of garment contacting adhesive and adhesive protection sheets on the outwardly facing, underside surface (not shown) of the backsheet 66, both in the wing regions 68 and also along the central longitudinal direction of the pad.

Between the liquid pervious topsheet layer 62 and the liquid impervious backsheet layer (outercover) 66 is positioned one or more interiorly-situated layers 64, 65. For example, as illustrated, the pad includes an absorbent core layer 64. The absorbent core layer 64 functions to absorb and preferably "lock-up" and retain the bodily fluids that pass into the absorbent article 60 through the topsheet layer 62. The absorbent core layer 64 can comprise a single layer or multiple layers and these one or more layers can themselves comprise similar or different materials. In order to efficiently and effectively utilize the absorbent capacity of the article, it is common for the absorbent structure to include one or more surge layers, liquid distribution layers or wicking layers 65 in combination with a highly absorbent core layer 64 that preferentially absorbs and retains the liquids. Suitable wicking layers include, but are not limited to, bonded-carded webs, hydroentangled nonwoven webs, or spunbond webs containing fibers treated with or containing one or more topical agents that improve the contact angle with the bodily fluid and/or modify the flow properties of the bodily fluid. Highly absorbent core layers 64 often include, but are not limited to, batts or webs containing wood pulp fibers, superabsorbent particles (also known as SAP or SAM), synthetic wood pulp fibers, synthetic fibers and combinations thereof. The absorbent core layer may comprise any one of a number of materials and structures, the particular selection of which will vary with the desired loading capacity, flexibility, body fluid to be absorbed and other factors known to those skilled in the art. By way of example, suitable materials and/or structures for the absorbent core layer include, but are not limited to, those described in U.S. Pat. No. 4,610,678 to Weisman et al.; U.S. Pat. No. 6,060,636 to Yahiaoui et al.; U.S. Pat. No. 6,610,903 to Latimer et al.; U.S. Pat. No. 7,358,282 to Krueger et al. and United States patent publication 20100174260 to Di Luccio et al., each of which is hereby incorporated by reference thereto in its entirety.

The shape of the absorbent core layer 64 can vary as desired and can comprise any one of various shapes including, but not limited to, generally triangular, rectangular, dog-bone and elliptical shapes. In one embodiment, the absorbent core layer 64 has a shape that generally corresponds with the overall shape of the sanitary pad 60 such that the absorbent core layer 64 terminates proximate the peripheral seal region 70 and wings 68. The dimensions of the absorbent core layer can be substantially similar to those of the sanitary pad 60; however it will be appreciated that the dimensions of the absorbent core layer 64 while similar, will often be slightly less than those of the overall sanitary pad 60 in order to be adequately contained therein, and desirably sealed around it's edges.

As previously indicated, the absorbent core layer 64 is positioned between the topsheet layer 62 and backsheet 66 layer. The individual layers comprising the article can be attached to one another using means known in the art such as adhesive, heat/pressure bonding, ultrasonic bonding and other suitable mechanical attachments. Commercially available construction adhesives usable in the present invention include, for example Rextac adhesives available from Huntsman Polymers of Houston, Tex., as well as adhesives available from Bostik Findley, Inc., of Wauwatosa, Wis. In one embodiment, the absorbent core layer 64 can be sealed between the topsheet layer 62 and backsheet layer 66 along the perimeter of the absorbent core layer 64 along sealing region 70 formed by the application of heat and pressure to melt thermoplastic polymers located in the topsheet layer 62 and/or backsheet layer 66.

The wings 68 can be constructed from materials described above with respect to the topsheet layer and backsheet layer. In one embodiment, the wings can comprise an extension of a layer of material within the topsheet layer and/or backsheet layer. By way of example, the wings 68, can be formed by an extension of the topsheet layer 62 and backsheet layer 66 that are welded together along sealing region 70. Such wings can be integrally formed with the main portion of the absorbent article. Alternatively, the wings can be formed independently and separately attached to an intermediate section of the article. Wings that are made independent of the other components of the absorbent article can be welded onto or adhesively joined to a portion of the topsheet layer and/or backsheet layer. In addition, as is known in the art, when cutting materials to the desired shape it is preferable to arrange the components so as to minimize waste. Examples of processes for manufacturing absorbent articles and wings include, but are not limited to those described in U.S. Pat. No. 4,059,114 to Richards; U.S. Pat. No. 4,862,574 to Hassim et al., U.S. Pat. No. 5,342,647 to Heindel et al., U.S. Pat. No. 7,070,672 to Alcantara et al., international publication WO1997040804 to Emenaker et al., and United States patent publication 20040040650 to Venturino et al., each of which are hereby incorporated by reference thereto in its entirety.

As noted, in order to further assist with the maintenance of the sanitary pad 60 in the desired location on the undergarment, garment adhesive (not shown) may be applied to the garment facing side of the backsheet layer 66 (not shown). The use of garment adhesive on the backsheet to help secure placement of an absorbent article on the garment is well known in the art and there are numerous adhesive patterns and releasable peel strips suitable for use with the present invention. Examples of suitable garment adhesives, patterns and release sheets include, but are not limited to, those described in DE700225U1; U.S. Pat. No. 3,881,490 to Whitehead et al.; U.S. Pat. No. 3,913,580 Ginocchio; U.S. Pat. No. 4,337,772 to Roeder et al.; GB1349962; and United States patent publication 20070073255A1 to Thomas et al., each of which are hereby incorporated by reference thereto in its entirety.

Figure 3A:
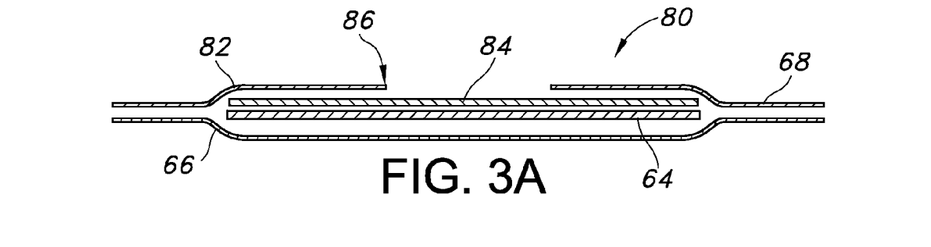
FIG. 3A is a stylistic cross-sectional view of the feminine sanitary pad of FIG. 3 taken along line 3A-3A of FIG. 3.
Figure 4:
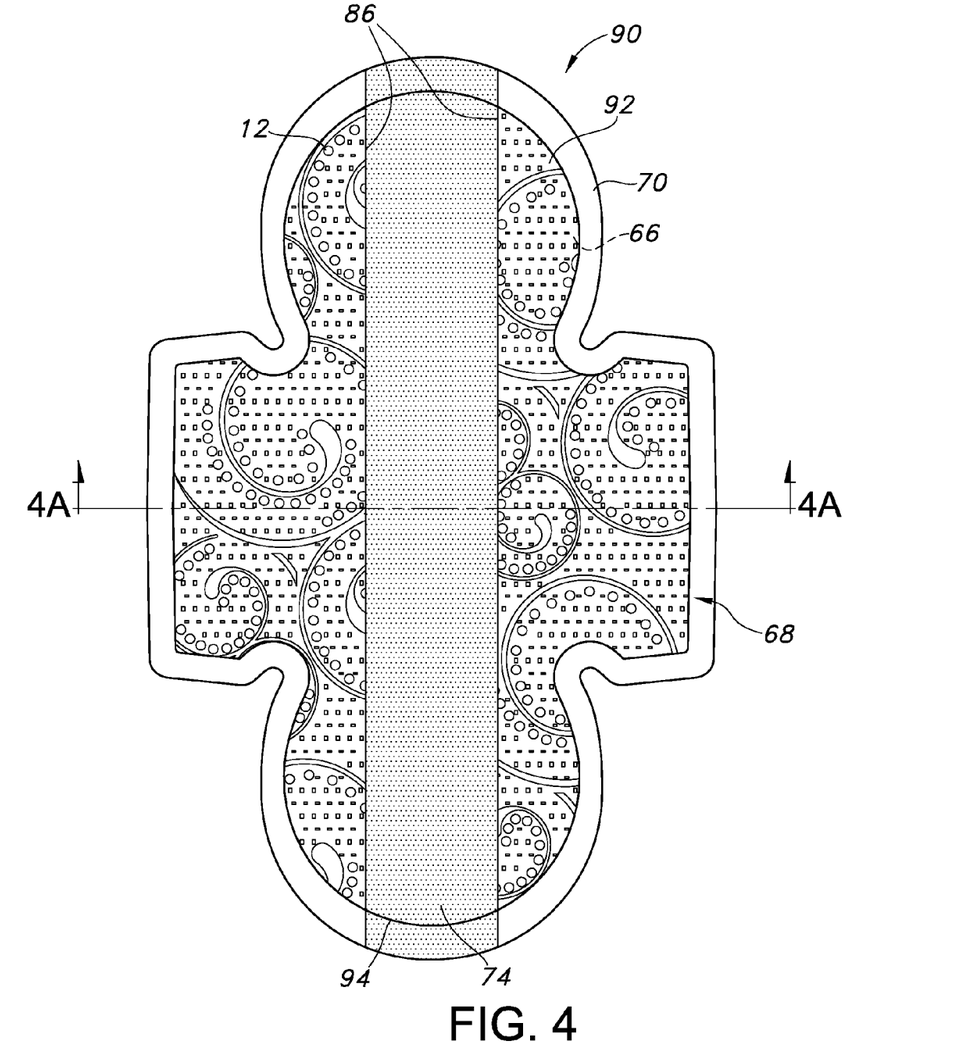
FIG. 4 is a top plan view of yet another alternative embodiment of a feminine sanitary pad in accordance with the invention.
Figure 4A:
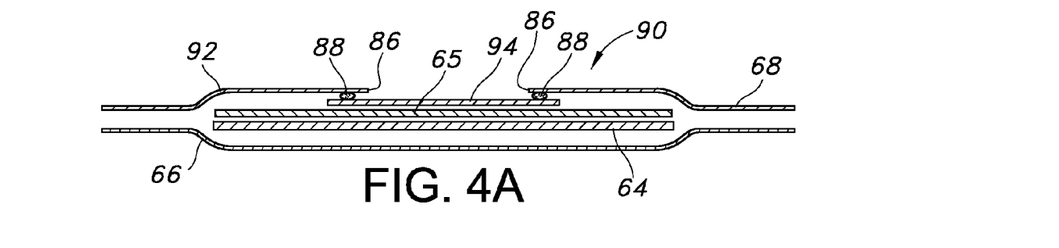
FIG. 4A is a stylistic cross-sectional view of the feminine sanitary pad of FIG. 4 taken along line 4A-4A of FIG. 4.

In an alternative embodiment of a sanitary pad 80 in accordance with the invention, a top plan view of a sanitary pad with a multiple or dual-layer topsheet is illustrated in FIGS. 3 and 3A. In particular, a stylized cross-sectional view of the sanitary pad of FIG. 3 at line 3A-3A, is illustrated in FIG. 3A. As can be seen in the figures, the sanitary pad includes a two layer topsheet having side cover topsheet layers 82 positioned along the longitudinal side edges of the pad, and a subjacent central topsheet layer 84 positioned between the side cover topsheet layers 82 and the absorbent core layer 64. While shown as extending the full width dimension of the absorbent core, such subjacent central topsheet layer 84 need not run the full width, but instead may only extend slightly under the side cover topsheet layers edges 86. The side cover topsheet layers 82 may be bonded to such subjacent central topsheet layer by any known bonding method, such as for example by adhesive, thermal or ultrasonic bonding processes. Such a two layer topsheet offers the benefit of having a first desired material along the pad's longitudinal side edges and another different desired material along the pad's central longitudinal direction 74. For example, it may be desirable to have a soft fibrous nonwoven topsheet material placed along the pad's longitudinal side edges to assist in reducing abrasion with a user's inner thighs during use and to provide additional comfort. In contrast, an apertured film may be desirable as a subjacent central topsheet layer 84, to assist in reducing stain appearance and rewet concerns at the center of the pad, where pad soiling would be likely.

In yet another alternative embodiment of a sanitary pad 90 in accordance with the invention, a top plan view and companion stylistic cross-sectional view are illustrated in FIGS. 4 and 4A. As can be seen in these figures, a two layered topsheet is also illustrated. However, in this instance, the inventive topsheet layer material is used as side cover topsheet layers 92. A different topsheet material, such as a different film or nonwoven sheet material is used for placement along the central longitudinal direction 74 of the pad, as a central topsheet layer 94 subjacent to the side cover topsheet layers 92. As illustrated, a line of adhesive 88 secures the side cover topsheet layers 92 to the subjacent central topsheet layer 94 beneath side edges 86. The subjacent central topsheet layer 94 is shown as not spanning the full width of either a transfer layer 65 or absorbent core layer 64 positioned beneath it.

The absorbent articles/sanitary pads of the present invention may further include one or more components or elements as may be desired. By way of example, the absorbent article may optionally include slits, voids or non-coordinated embossing on the topsheet layer, interior layers, and/or absorbent core layer, in order to improve fluid intake, fluid distribution, stiffness (bending resistance) and/or aesthetic appeal. Examples of additional suitable embossing patterns and methods of embossing include, but are not limited to, those are described in U.S. Pat. No. 4,781,710 Megison et al.; U.S. Pat. No. 7,686,790 to Rasmussen et al., EP0769284A1 to Mizutani et al.; and United States publication 20050182374 to Zander et al., each of which are hereby incorporated by reference thereto in its entirety.

The contemplated personal care absorbent articles can optionally contain one or more additional elements or components as are known and used in the art including, but not limited to, the use of fold lines, individual wrappers, elasticated flaps that extend above the plane of the topsheet layer in use, additional independent wings such as about the ends, odor control agents, perfumes, and the use of ink printing on one or more surfaces of the topsheet layer, backsheet layer, wings, interiorly-situated layer(s) and/or absorbent core layer. Still further additional features and various constructions are known in the art.

By including the inventive topsheet layer material as the topsheet layer in absorbent articles, targeted absorbent/fluid capture regions can be created, as such aperture and embossing fluid management features are in close proximity to one another, functioning as a drain-like feature. Further, by visually and spatially coordinating at least a first series of apertures having a curvilinear overall shape configuration with an embossed feature (such as a channel or series of channels) having a similar or identical curvilinear overall shape configuration, a visual cue as to areas of absorbency/fluid capture can be provided to consumers of such absorbent products. Such visually distinctive regions can be placed in certain areas of consumer products to enable proper placement of such articles in a consumer's undergarments or under likely soiling locations.

Thus, while the invention has been described in detail with respect to specific embodiments and/or examples thereof, it will be apparent to those skilled in the art that various alterations, modifications and other changes may be made to the invention without departing from the spirit and scope of the same. It is therefore intended that the claims cover or encompass all such modifications, alterations and/or changes.

The invention claimed is:

1. A topsheet layer material with coordinated apertures and embossed channel, said topsheet layer material including a longitudinal direction, a transverse direction and a depth direction, said topsheet layer material including at least one embossed channel wherein said embossed channel includes multiple side edges, and a first series of apertures, wherein said at least one embossed channel has a curvilinear overall shape configuration along either said longitudinal direction, said transverse direction or a combination of longitudinal and transverse directions, and wherein said first series of apertures are positioned in an uninterrupted sequence on said topsheet layer material laterally adjacent said at least one embossed channel along each of said multiple side edges, such that said first series of apertures are configured in the same or similar overall shape configuration as at least one embossed channel overall shape configuration.

2. The topsheet layer material of claim 1, wherein said embossed channel includes a side edge and said first series of apertures are present in increasing size adjacent said embossed channel side edge.

3. The topsheet layer material of claim 2, wherein larger size apertures are positioned closest to said embossed channel side edge.

4. The topsheet layer material of claim 1, wherein said first series of apertures extend beyond at least two side edges of said embossed channel.

5. The topsheet layer material of claim 1, further including a second set of apertures.

6. The topsheet layer material of claim 1 wherein said embossed channel overall shape configurations are circular swirls.

7. The topsheet layer material of claim 1, wherein apertures straddle two side edges of an embossed channel overall shape configuration.

8. The topsheet layer material of claim 1, wherein said embossed channel overall shape configuration has an end and said first series of apertures surround said end of said embossed channel overall shape configuration.

9. The topsheet layer material of claim 1, wherein said embossed channel defines a width and apertures are positioned on an embossed channel overall shape configuration and extend beyond the width of said embossed channel overall shape configuration.

10. The topsheet layer material of claim 1, wherein apertures are positioned completely around said embossed channel overall shape configuration.

11. An absorbent article comprising the topsheet layer material of claim 1.

12. The absorbent article of claim 11, wherein said article includes a central longitudinal section, and at least two edges of said embossed channel is positioned along said article central longitudinal section.

* * * * *